United States Patent
Maierhofer

(10) Patent No.: US 11,324,868 B2
(45) Date of Patent: May 10, 2022

(54) DEVICE FOR EXTRACORPOREAL BLOOD TREATMENT AND DEVICE FOR COLLECTING BLOOD CLOTS, AND METHOD FOR DETERMINING A HEMODYNAMIC PARAMETER DURING AN EXTRACORPOREAL BLOOD TREATMENT

(71) Applicant: FRESENIUS MEDICAL CARE DEUTSCHLAND GMBH, Bad Homburg (DE)

(72) Inventor: Andreas Maierhofer, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 284 days.

(21) Appl. No.: 16/619,476

(22) PCT Filed: Jun. 7, 2018

(86) PCT No.: PCT/EP2018/065057
§ 371 (c)(1),
(2) Date: Dec. 5, 2019

(87) PCT Pub. No.: WO2018/224603
PCT Pub. Date: Dec. 13, 2018

(65) Prior Publication Data
US 2020/0139033 A1 May 7, 2020

(30) Foreign Application Priority Data
Jun. 10, 2017 (DE) ...................... 10 2017 005 535.1

(51) Int. Cl.
*A61M 1/16* (2006.01)
*A61M 1/26* (2006.01)
*A61M 1/36* (2006.01)

(52) U.S. Cl.
CPC ........ *A61M 1/1605* (2014.02); *A61M 1/1621* (2014.02); *A61M 1/267* (2014.02);
(Continued)

(58) Field of Classification Search
CPC .. A61M 1/1605; A61M 1/1621; A61M 1/267; A61M 1/3639; A61M 1/3663;
(Continued)

(56) References Cited

U.S. PATENT DOCUMENTS 5,830,365 A   11/1998  Schneditz
9,415,151 B2   8/2016  Schlaeper et al.
(Continued)

FOREIGN PATENT DOCUMENTS

DE   19528907 C1   11/1996
WO   2010121743 A1   10/2010
(Continued)

OTHER PUBLICATIONS

International Search Report and Written Opinion issued in corresponding International Patent Application No. PCT/EP2018/065057 (with English translation of International Search Report) dated Sep. 6, 2018 (21 pages).
(Continued)

*Primary Examiner* — Krishnan S Menon
(74) *Attorney, Agent, or Firm* — Kilyk & Bowersox, P.L.L.C.

(57) ABSTRACT

The invention relates to an apparatus for extracorporeal blood treatment, comprising a blood treatment unit 1 that comprises at least one compartment 3. The invention further relates to an apparatus 15A, 15B for collecting blood clots for a blood line 5, 7 for supplying blood to or removing blood from a blood treatment unit 1 of an extracorporeal blood treatment apparatus, and to a method for determining a hemodynamic parameter during extracorporeal blood
(Continued)

Figure 1:
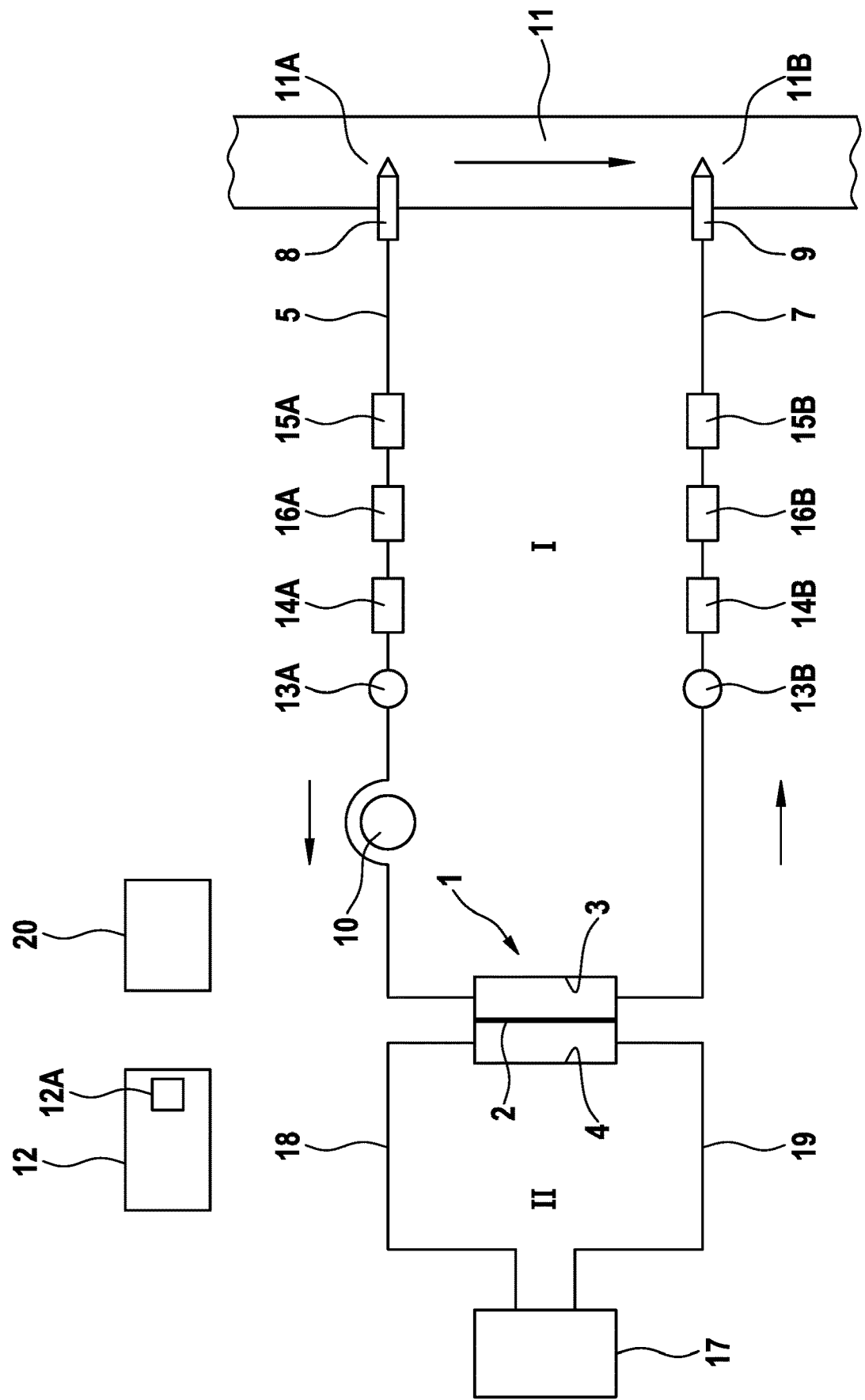

treatment using an extracorporeal blood treatment apparatus. In order to determine the hemodynamic parameter, the conveying direction of the blood pump 10 is reversed from a "normal" blood flow to a "reversed" blood flow. It has been found in practice that, in the event of a reversal in the conveying direction of the blood pump in order to carry out a measurement for determining a hemodynamic parameter, there is a risk of blood clots reaching the patients, although the dialyser traps blood clots. The apparatus according to the invention provides an apparatus 15A for catching blood clots, at least in the blood line of the extracorporeal blood circuit I that leads to the blood treatment unit 1 during a "normal blood flow". The blood treatment unit traps blood clots during blood treatment having a "normal" blood flow. In the case of a "reversed" blood flow, the apparatus for catching blood clots in the blood line that leads to the blood treatment unit 1 during a "normal blood flow" traps blood clots that may have previously accumulated at the inlet of the blood treatment unit.

21 Claims, 4 Drawing Sheets

(52) U.S. Cl.
CPC ........ *A61M 1/3639* (2013.01); *A61M 1/3663* (2013.01); *A61M 2205/18* (2013.01); *A61M 2205/3368* (2013.01)

(58) Field of Classification Search
CPC ...... A61M 2205/18; A61M 2205/3368; A61M 60/50; A61M 2205/7545; A61M 1/3658; A61M 1/3635
See application file for complete search history.

(56) References Cited

U.S. PATENT DOCUMENTS

| | | |
|---|---|---|
| 2010/0270230 A1 | 10/2010 | Brueckner et al. |
| 2010/0274172 A1 | 10/2010 | Guenther et al. |
| 2013/0155387 A1 | 6/2013 | Wiktor |
| 2015/0021244 A1 | 1/2015 | Furuhashi et al. |

FOREIGN PATENT DOCUMENTS

| | | |
|---|---|---|
| WO | 2010121750 A1 | 10/2010 |
| WO | 2012022456 A1 | 2/2012 |
| WO | 2018001996 A1 | 1/2018 |

OTHER PUBLICATIONS

International Preliminary Report on Patentability issued in corresponding International Patent Application No. PCT/EP2018/065057 dated Dec. 10, 2019 (English translation) (11 pages).

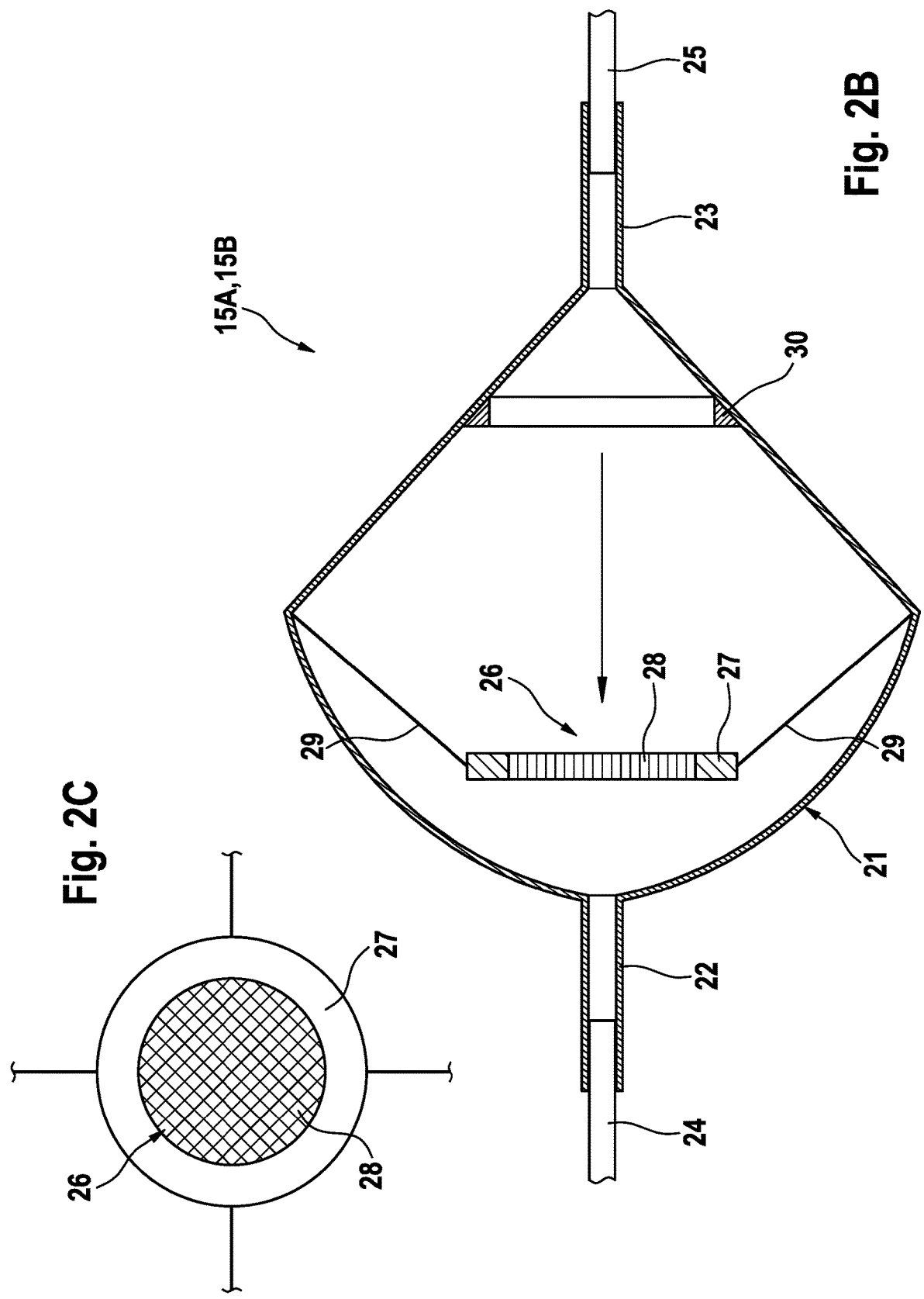

DEVICE FOR EXTRACORPOREAL BLOOD TREATMENT AND DEVICE FOR COLLECTING BLOOD CLOTS, AND METHOD FOR DETERMINING A HEMODYNAMIC PARAMETER DURING AN EXTRACORPOREAL BLOOD TREATMENT

This application is a National Stage Application of PCT/EP2018/065057, filed Jun. 7, 2018, which claims priority to German Patent Application No. 10 2017 005 535.1, filed Jun. 10, 2017.

The invention relates to an apparatus for extracorporeal blood treatment, comprising a blood treatment unit that comprises at least one compartment. The invention further relates to an apparatus for collecting blood clots for a blood line for supplying blood to or removing blood from a blood treatment unit of an extracorporeal blood treatment apparatus, and to a method for determining a hemodynamic parameter during extracorporeal blood treatment using an extracorporeal blood treatment apparatus.

In methods for chronic blood purification therapy, such as hemodialysis, hemofiltration and hemodiafiltration, blood is guided through an extracorporeal blood circuit. In hemodialysis, the blood to be treated flows through the blood chamber of a dialyser that is divided into the blood chamber and a dialysate chamber by a semi-permeable membrane, while dialysate flows through the dialysate chamber of the dialyser in a dialysate system. The extracorporeal blood circuit comprises an arterial hose line, which leads to the blood chamber, and a venous hose line, which leads from the blood chamber. The known blood treatment apparatuses have a blood pump, which is generally arranged upstream of the blood chamber of the dialyser in order to ensure sufficient blood flow in the extracorporeal blood circuit.

An arteriovenous fistula is often applied surgically as an access to the patient's blood vessel system. The use of an implant is also possible. The perfusion of the fistula is important for the functioning thereof. If the fistula flow falls below a critical value, the risk of a fistula thrombosis increases with the possible loss of vascular access, which is a significant complication in dialysis treatment (W. Bay et al.: Color Doppler flow predicts PTFE graft failure, J. Am. Soc. Nephrol. 5: 407 (1994)). If the fistula flow during dialysis treatment is lower than the extracorporeal blood flow ($Q_B$), local fistula recirculation results, a fraction of the dialysed blood that is returned to the fistula by the venous blood line being returned to the dialyser via the arterial blood line. The fistula recirculation ($R_A$) causes a significant reduction in the dialysis efficiency (F. Gotch: "Models to predict recirculation and its effect on treatment time in single-needle dialysis" First Intl. Symposium on Single-Needle Dialysis, ed.: S. Rignoir. R. Vanholder and P. Invanovich, Cleveland, ISAO Press, 1984, page 305 ff.).

On account of the clinical importance thereof, various methods are known for determining the blood flow in the vascular access (shunt flow) or for determining the recirculation. Many methods are based on a physical or chemical characteristic variable of the blood, which characteristic variable is changed in the extracorporeal blood circuit. The physical or chemical characteristic variable may for example be the temperature, density or electrolyte composition of the blood. The characteristic variable can be directly or indirectly changed in the extracorporeal blood circuit by modifying a physical or chemical characteristic value in the dialysate system.

A method referred to as thermodilution, for measuring shunt flow, is known from EDTNA-ERCA Journal 19, 6 (1993). In this known method, a brief temperature drop in the dialysate system is triggered, which temperature drop is transferred to the venous branch of the extracorporeal circuit and leads to a detectable temperature increase in the arterial branch of the extracorporeal circuit if recirculation occurs.

DE 195 28 907 C1 discloses a method for determining the cardiopulmonary recirculation, which method is based on two successive measurements of the recirculation fraction that are carried out before and after the reversal of the blood flow in the extracorporeal circuit. A reversal of the blood flow can in principle result from swapping the arterial and venous patient connections. However, manually swapping the patient connections is not without problems in terms of hygiene and safety considerations. Therefore, numerous apparatuses for blood hose systems have been developed which cause an automatic reversal of the flow direction by means of crosswise connection of the relevant hose line portions of the hose line system. In the process, however, the flow direction in the part of the extracorporeal circuit that includes the dialyser is maintained. Therefore, the protection systems located in this part can be used both before and after the reversal of the blood flow.

A valve means for automatic reversal of the flow direction is known from WO 2014/074231 A1 for example.

DE 195 28 907 C1 proposes, as an alternative to the known valve means for automatic reversal of the flow direction, simply reversing the conveying direction of the blood pump in the extracorporeal blood circuit. However, this option has not yet been used in practice, since operating an extracorporeal blood treatment apparatus comprising a dialyser through which blood flows in different directions has been found to be not without problems in terms of safety considerations.

The object of the invention is to allow a hemodynamic parameter to be measured without using the known valve means for automatic reversal of the flow direction which cause an automatic reversal of the flow direction by means of crosswise connection of the relevant hose line portions of the hose line system.

This object is achieved by the features of the independent claims. The dependent claims relate to preferred embodiments of the invention.

The apparatus for extracorporeal blood treatment according to the invention comprises:
a blood treatment unit that comprises at least one compartment,
a first blood line that is connected to a connection of the compartment and comprises a first patient connection,
a second blood line that is connected to a connection of the compartment and comprises a second patient connection,
a blood pump for conveying blood,
a device for measuring a physical or chemical characteristic variable,
a control and evaluation unit that is connected to the blood pump and to the device for measuring a physical or chemical characteristic variable, and is designed such that the blood pump is operated in a first operating mode having a normal blood flow, such that blood flows from the first patient connection to the blood treatment unit and from the blood treatment unit to the second patient connection,
the blood pump is operated in a second operating mode having a reversed blood flow, such that blood flows from the second patient connection to the blood treatment unit and from the blood treatment unit to the first patient connection, and
the hemodynamic parameter is determined from the measured physical or chemical characteristic variable, at least in the case of a reversed blood flow. In order to prevent the formation of blood clots in the extracorporeal blood circuit, an anticoagulant substance, usually heparin, is often administered, either continuously during dialysis or as an initial bolus. Said substance is usually added upstream of the dialyser. In addition to the systematic effect of the anticoagulant substance in the patient, a possible mode of action is also the accretion of said substance on the surfaces of the extracorporeal system, in particular on the lumen of the dialyser fibres.

The dialyser used in extracorporeal blood treatment is an insurmountable obstacle for the clots on account of the diameter of the hollow fibres of less than 0.2 mm. Therefore, clots forming upstream of the dialyser cannot reach the region downstream of the dialyser and thus cannot reach the patients. However, blood clots located downstream of the dialyser can be infused. This is independent of the flow direction of the blood through the dialyser.

In the known blood treatment apparatuses, clots that form in the blood on the way from the dialyser to the patient are generally trapped by an apparatus for catching blood clots that is provided downstream of the dialyser in the venous blood line of the extracorporeal hose system, before the venous cannula. This apparatus is also referred to as a blood clot catcher.

It has been found in practice that, in the event of a reversal in the conveying direction of the blood pump in order to carry out a measurement for determining a hemodynamic parameter, there is a risk of blood clots reaching the patient, although the dialyser traps blood clots that form upstream of the dialyser. It has been found in practice that, during operation having a "normal" blood flow, blood clots accumulate at the inlet of the dialyser. In the event of a reversal of the blood flow, these blood clots are then flushed towards the patient.

The apparatus for extracorporeal blood treatment according to the invention therefore provides an apparatus for catching blood clots, at least in the first blood line. During blood treatment having a "normal" blood flow, a second apparatus for catching blood clots, which may be provided in the second blood line, can trap blood clots that form downstream of the dialyser. In the case of a "reversed" blood flow, the apparatus for catching blood clots in the first blood line traps the blood clots that may have previously accumulated at the inlet of the blood treatment unit. As a result, there is no risk of infusion of blood clots when the conveying direction of the blood pump is switched from a "normal" blood flow to a "reversed" blood flow in order to determine the hemodynamic parameter.

It is of no relevance to the invention which hemodynamic parameters are determined on the basis of one or more measurements during a reversed blood flow, and how the hemodynamic parameters are determined. It is also irrelevant whether variables on the blood side or on the dialysate side are measured. Instead of the physical or chemical property of the blood in the blood line, a characteristic variable in the dialysate that correlates with the physical or chemical characteristic variable in the blood line can also be measured. In this respect, the invention relates to all methods in which a chemical or physical characteristic variable is measured before and after the reversal of the flow direction or only when the blood flow is reversed, in order to determine the hemodynamic parameters.

For example, the invention relates to all methods in which a chemical or physical characteristic variable in the blood in one branch of the extracorporeal blood circuit changes before and after the reversal of the flow direction, and in which the change in the chemical or physical characteristic variable in the blood in another branch of the extracorporeal blood circuit or in the dialysate that results from the change in the chemical of physical characteristic variable in said first branch is detected.

In order to determine the hemodynamic parameter, the progression of the observed temporal change in the physical or chemical characteristic variable in the line system on the blood side or on the dialysate side can be measured. A specific application is in determining the recirculation according to the known methods that require a reversal of the flow direction. In this case, the hemodynamic parameter can be the recirculation in the fistula or the shunt flow.

The blood treatment unit can be any unit for carrying out hemodialysis, hemofiltration, hemodiafiltration, apheresis, or the like. In the case of hemodialysis, hemofiltration or hemodiafiltration, the blood treatment unit (dialyser) comprises a first and a second compartment that are separated from one another by a semi-permeable membrane. If, in contrast, the blood treatment is not based on diffusive or convective substance exchange, for example on adsorption on functionalised surfaces, a second compartment is not required.

The method according to the invention provides for blood clots that have formed in the blood upstream of the compartment of the blood treatment unit before the reversal of the flow direction of the blood to be trapped by an apparatus for catching blood clots in the first blood line following the reversal of the flow direction of the blood.

Furthermore, it has been found in practice that the first apparatus for catching blood clots in the first blood line causes an increase in the flow resistance in the case of a "normal" blood flow. This is disadvantageous in that the first apparatus for catching blood clots is actually not required for the "normal" blood flow, since the blood clots are already trapped effectively by the blood treatment unit.

One embodiment therefore provides a flow direction-dependent apparatus for catching blood clots. In the preferred embodiment, at least one of the two apparatuses for catching blood clots is flow direction-dependent. In particular, the first apparatus for catching blood clots that is provided upstream of the dialyser in the case of a "normal" blood flow is at least fully operational only when the flow direction is reversed. Otherwise, the flow of the blood through the apparatus for catching blood clots is at least not significantly impeded. Therefore, not only is an increase in the flow resistance of the blood prevented, but the risk of degradation of the blood or the creation of stagnation points, which in turn can lead to the formation of blood clots, is reduced. In one embodiment, the apparatus for collecting blood clots comprises a housing body having a first connection and a second connection, and a screen body for catching the blood clots that is arranged between the two connections in the flow path of the blood. The screen body can be designed in various ways, provided that blood clots are trapped effectively. Such filter screens belong to the prior art. The apparatus for collecting blood clots is designed such that a flow path bypassing the screen body forms in the housing body when blood does not flow in at the first connection and out at the second connection, in the "normal" flow direction, but instead flows in at the second connection and out at the first connection, in the "reversed" flow direction. Since at least part of the blood flow bypasses the screen body, the flow resistance is reduced. When blood flows in at the first connection and out at the second connection, in the "normal" flow direction, however, a flow path bypassing the screen body does not form in the housing body. In this flow direction, the apparatus can trap the blood clots effectively.

A further embodiment provides for the screen body to be designed as a valve body and for a valve seat for the screen body to be formed in the housing body. The screen body is movably arranged in the housing body so as to rest on the valve seat when blood flows in at the first connection and out at the second connection, in the "normal" flow direction, and so as to be lifted off the valve seat when blood flows in at the second connection and out at the first connection, such that a flow path bypassing the screen body forms in the housing body. The movement of the valve body can be caused simply by the dynamic pressure when the blood flows towards the valve body.

Resting of the screen body on the valve seat in just one flow direction can be achieved by a particular shape of the housing and/or the restriction of the range in which the screen body can move in the housing body.

In one embodiment, the screen body is movably arranged between the first and second connection in the flow path of the blood, the movement of the screen body in the housing body being restricted to a range between a first and a second end position. The restriction of the movement range of the screen body between the first and second connection in the flow path of the blood can be achieved by at least one elongate, flexible fixing element, one end of which is connected to the screen body and the other end of which is connected to the housing body. In a preferred embodiment, a plurality of elongate, flexible fixing elements are provided, which elements are arranged around the periphery of the screen body. As a result, the screen body can be adequately fixed from all sides centrally in the middle of the housing body, the blood being able to flow unimpeded between the fixing elements and through the housing body when the screen body is not resting on the valve seat.

A further embodiment provides for the housing body to have a circular cross section and for the screen body to comprise a retaining part having a circular cross section, in which part the screen is inserted. The screen can be designed as a planar, discoid body or in the shape of a thimble. The thimble-shaped design of the screen has the advantage of a larger surface. As a result, the screen cannot become blocked as quickly.

The first and second connection of the apparatus for catching blood clots can be designed as a connector part of a luer or a luer lock connector, for example, in order to be able to connect the apparatus to the corresponding hose line portions of the blood hose system or of the patient connections (puncture cannulas). In this case, the apparatus for catching blood clots can be provided together with the blood hose system or without the blood hose system. The apparatus for catching blood clots can be a component of the hose line of the blood hose system or of the puncture cannula. For example, the connections can be adhesively bonded or welded to the hose line or the cannula.

In one embodiment, a first apparatus for collecting blood clots is provided in the first blood line, and a second apparatus for collecting blood clots is provided in the second blood line.

When the portion of the first blood line connected to the first patient connection is connected to the second connection of the housing body of the first apparatus for collecting blood clots, and the portion of the first blood line connected to the connection of the blood treatment unit is connected to the first connection of the housing body of the first apparatus for catching blood clots, the blood can flow past the filter screen and through the first apparatus for catching blood clots in the "normal" flow direction. In the "reversed" flow direction, in contrast, the first apparatus traps blood clots.

When the portion of the second blood line connected to the blood treatment unit is connected to the first connection of the housing body of the second apparatus for collecting blood clots, and the portion of the second blood line connected to the second patient connection is connected to the second connection of the housing body of the second apparatus for collecting blood clots, the second apparatus traps blood clots in the "normal" flow direction. In the "reversed" flow direction, in contrast, the second apparatus does not trap blood clots.

In particular when the flow reversal does not occur until a late stage of the blood treatment, there is the risk that a relatively large amount of blood clots may have accumulated upstream of the blood treatment unit, which clots could clog the first apparatus for catching blood clots following a flow reversal. A further embodiment therefore provides a first pressure sensor for measuring the pressure in the first blood line, which sensor is connected to the control and evaluation unit such that the control and evaluation unit receives the measured values from the first pressure sensor. The control and evaluation unit is designed such that the pressure measured by the first pressure sensor in the second operating mode is compared with a predetermined threshold value. If the pressure measured by the first pressure sensor exceeds the predetermined threshold value, a signal indicating clogging of the apparatus is generated, which signal can trigger a further event. The threshold value may be an absolute threshold value that is stored in a memory of the control and evaluation unit, or may be a threshold value that is dependent on the blood flow and is calculated by the control and evaluation unit taking account of the predetermined blood flow rate.

In a further embodiment, the control and evaluation unit is designed such that the blood pump is switched from the "reversed" blood flow to the "normal" blood flow when the signal is generated. When clogging of the filter is detected, the control and evaluation unit can also prevent the flow reversal for the remainder of the blood treatment. In addition, a user control means can be designed such that the blocking of the flow reversal can be ended by a confirmation that possible blood clots have dissolved due to the administration of anticoagulants. An alarm unit and/or display unit can also be connected to the control and evaluation unit, such that the alarm unit and/or display unit receives the signal.

An alternative embodiment provides for a first pressure sensor for measuring the pressure in the first blood line and a second pressure sensor for measuring the pressure in the second blood line to be connected to the control and evaluation unit such that the control and evaluation unit receives the measured values from the first and second pressure sensor. In this embodiment, the control and evaluation unit is designed such that the pressure measured by the first pressure sensor in the second operating mode is compared with the pressure measured by the second pressure sensor in the first operating mode. If the pressure measured by the first pressure sensor exceeds the pressure measured by the second pressure sensor by a predetermined amount or factor, a signal is generated that indicates clogging. The pressure is measured by the first and second pressure sensor preferably at the same blood flow rate, and therefore the blood flow cannot have any influence on the monitoring of the apparatus for catching blood clots.

Figure 2A:
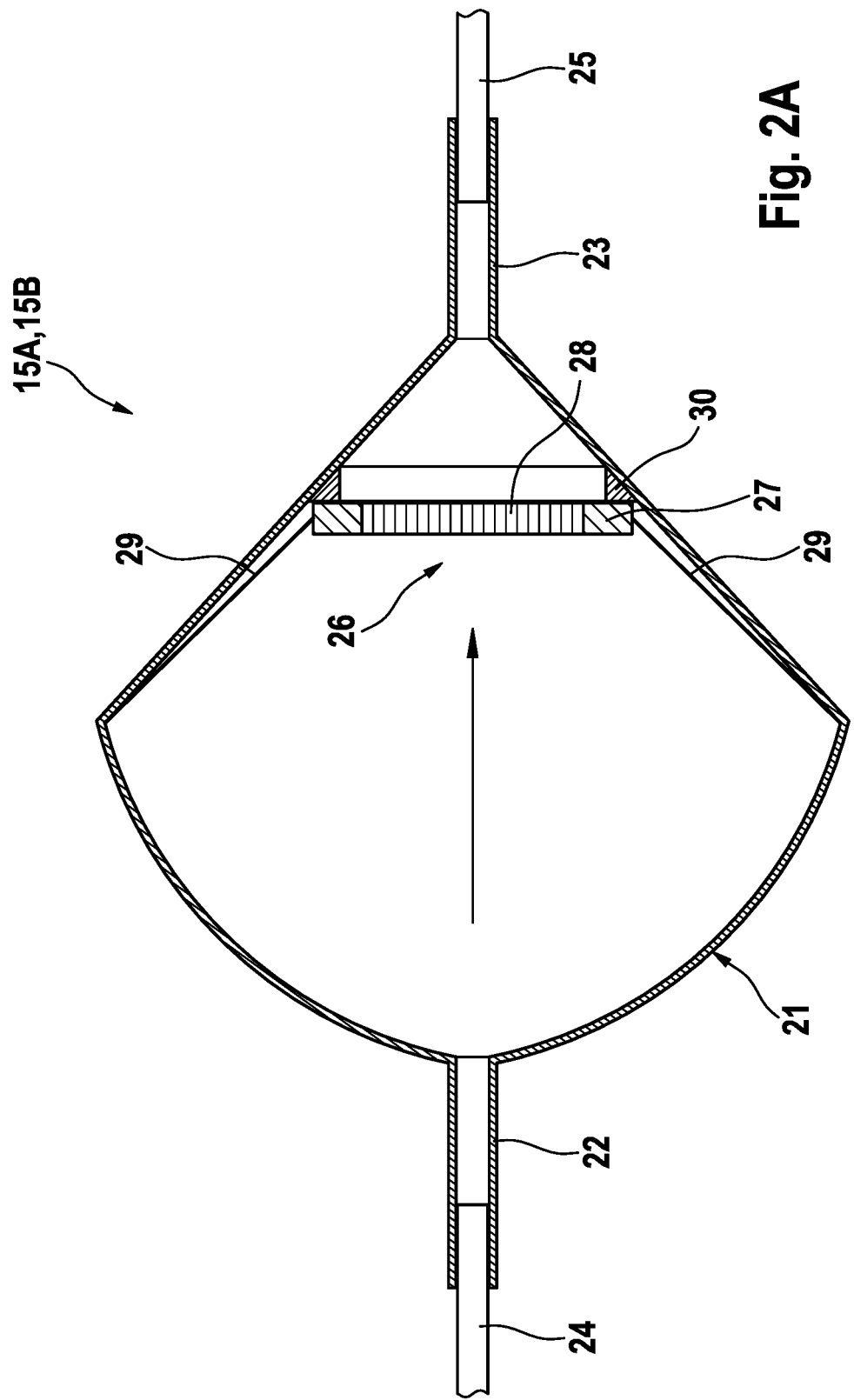
Figure 3A:
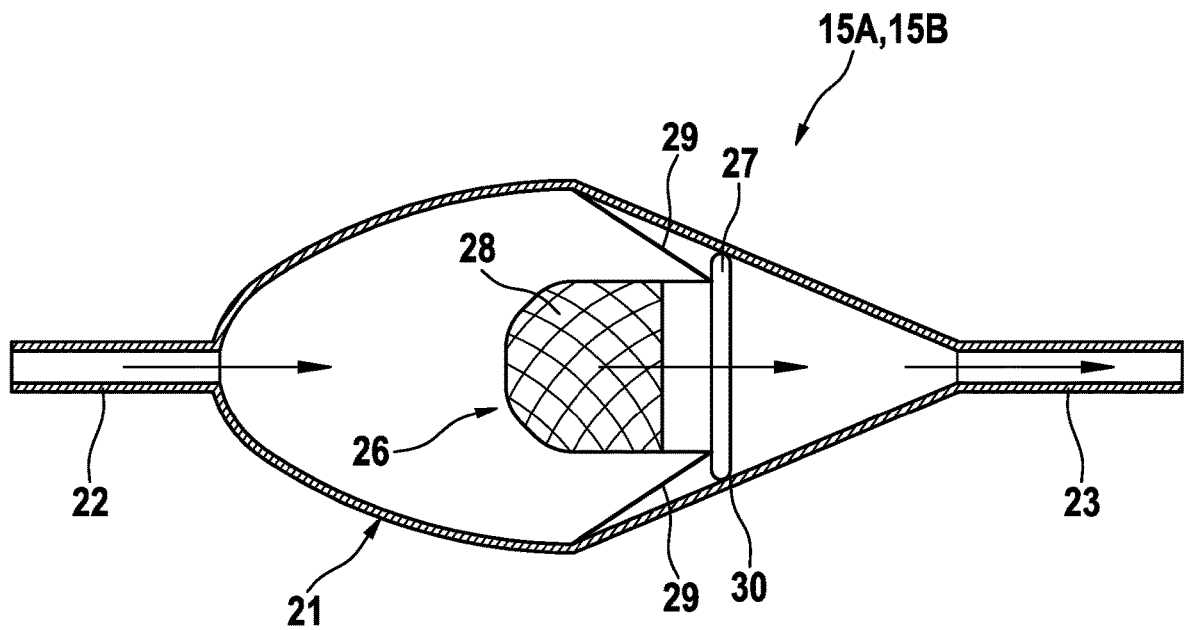
Figure 3B:
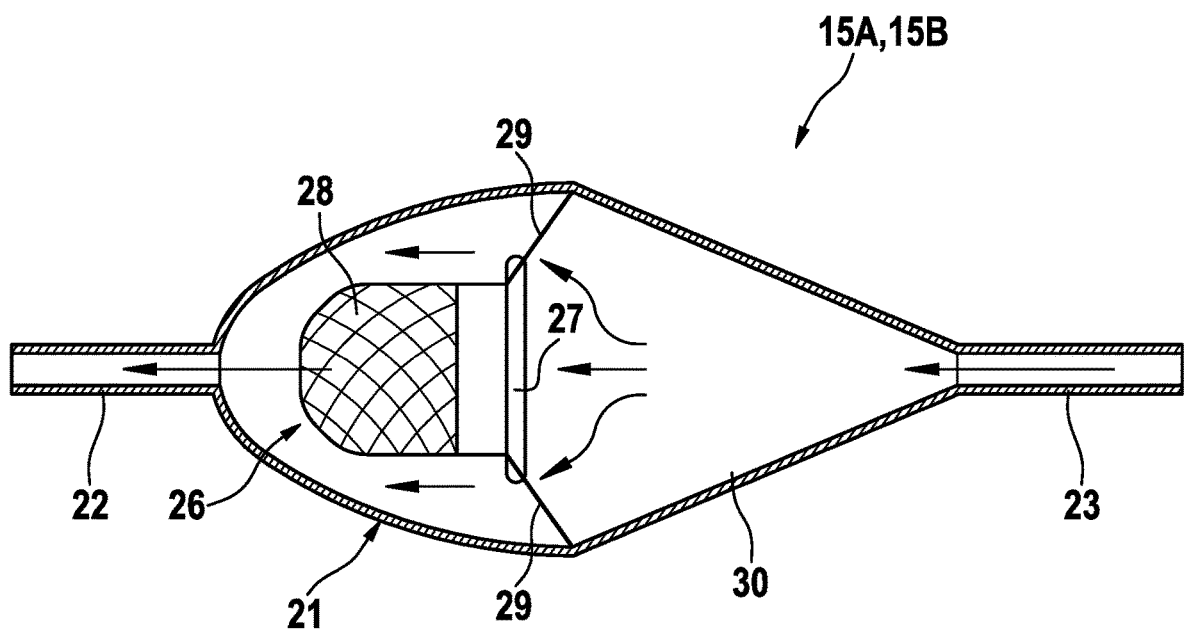

In the following, various embodiments of the invention are described in greater detail with reference to the drawings, in which:

FIG. 1 is a highly simplified schematic view of an embodiment of the apparatus according to the invention, FIG. 2A shows a first embodiment of an apparatus for catching blood clots in the flow direction, FIG. 2B shows a first embodiment of an apparatus for catching blood clots counter to the flow direction, FIG. 2C is a plan view of the screen body of the apparatus for catching blood clots, FIG. 3A shows a second embodiment of an apparatus for catching blood clots in the flow direction, and FIG. 3B shows a second embodiment of an apparatus for catching blood clots counter to the flow direction.

FIG. 1 is a highly simplified schematic view of those components of the extracorporeal blood treatment apparatus that are essential to the invention, which apparatus is a hemodialysis apparatus in the present embodiment. The blood treatment apparatus comprises a blood treatment unit 1, which may be a dialyser, that is divided into a first compartment 3 (blood chamber) and a second compartment 4 (dialysate chamber) by a semi-permeable membrane 2. The extracorporeal blood circuit I comprises a first blood line 5 that is connected to a first connection of the first compartment 3, the first compartment 3, and a second blood line 7 that is connected to a second connection of the first compartment 3. The first and second blood lines 5, 7 are hose lines of a blood hose system intended for single use (disposable). A first patient connection 8 (puncture cannula) is located at the end of the first blood line 5, and a second patient connection 9 (puncture cannula) is located at the end of the second blood line 7. The blood is conveyed by means of a blood pump 10 which is provided in the first blood line 5.

In order to carry out the blood treatment, the first puncture cannula 8 is connected to an upstream part 11A of the vascular access 11, while the second puncture cannula 9 is connected to a downstream part 11B of the vascular access 11, so that the patient's blood flows through the first blood line 5, the first compartment 3 of the blood treatment unit 3, and the second blood line 7. This case is referred to as "normal" blood flow. The blood pump 10 then conveys blood in the "normal" conveying direction. The upstream part 11A of the vascular access 11 is therefore the arterial part of the fistula, the first blood line 5 is the arterial blood line, the second blood line 7 is the venous blood line, and the downstream part 11B of the fistula is the venous part of the fistula.

For measuring the hemodynamic parameter, a reversal in the flow direction is required, such that the blood flows from the downstream part 11B of the vascular access 11, through the second blood line 7, the first compartment 3 of the blood treatment unit 1, and the first blood line 5, to the upstream part 11A of the vascular access 11. This case is referred to as "reversed" blood flow. The blood pump 10 then conveys blood in the "reversed" conveying direction.

The blood treatment apparatus comprises a central control and evaluation unit 12 for controlling all the components of the apparatus. The control and evaluation unit 12 can have, for example, a general processor, a digital signal processor (DSP) for continuously processing digital signals, a microprocessor, an application-specific integrated circuit (ASIC), an integrated circuit consisting of logic elements (FPGA) or other integrated circuits (IC) or hardware components, in order to perform the individual method steps for controlling the blood treatment apparatus. A data processing program (software) can run on the hardware components in order to carry out the method steps. A plurality or combination of the various components is also possible.

The control and evaluation unit 12 is designed such that the individual components of the blood treatment apparatus are actuated in order to carry out the blood treatment, and the measurements for determining a hemodynamic parameter of the blood treatment are carried out.

The blood treatment apparatus comprises a first pressure sensor 13A for measuring the pressure in the first blood line 5, between the blood pump 10 and the first patient connection 8, and a second pressure sensor 13B for measuring the pressure in the second blood line 7, between the first compartment 3 and the second patient connection 9.

The measurements for determining a hemodynamic parameter of the blood treatment can be carried out in the extracorporeal blood circuit I. A first measuring device 14A is provided for measuring a physical or chemical property of the blood in the first blood line, and a second measuring device 14B is provided for measuring a physical or chemical property of the blood in the second blood line. The pressure sensors 13A, 13B and the devices 14A, 14B for measuring a physical or chemical property of the blood are connected to the control and evaluation unit 12 by data lines (not shown).

A first apparatus 15A for catching blood clots is provided in the first blood line 5 between the first patient connection 8 and the first device 14A for measuring a physical or chemical property, and a second apparatus 15B for catching blood clots is provided in the second blood line 7 between the second device 14B for measuring a physical or chemical property and the second patient connection 9. The apparatuses 15A, 15B for catching blood clots are described in greater detail in the following, with reference to FIGS. 3A, 3B and 4A and 4B. The blood clot catchers 15A, 15B can, however, also be provided in other portions of the first and second blood line 5, 7.

Furthermore, the blood treatment apparatus comprises further monitoring and safety devices 16A, 16B that are merely indicated and that can function both in the "normal" and in the "reversed" flow direction. These monitoring and safety devices 16A, 16B include an air separation chamber, an air detector and a valve in the first and second blood line. The air separation chambers can have inlet and outlet lines that are arranged below the liquid level. Ultrasound sensors can be used for detecting air.

The dialysate system II comprises a device 17 for processing dialysate at a predetermined temperature. The fresh dialysate flows into the second compartment 4 via a dialysate feed line 18 and the used dialysate flows out of the second compartment 4 of the blood treatment unit 1 via a dialysate removal line 19 to the device 17 for processing dialysate. The device 17 for processing dialysate is connected to the control and evaluation unit 12 by a data line (not shown), and therefore the control and evaluation unit 12 can control the temperature and composition of the dialysate.

The measurements for determining a hemodynamic parameter of the blood treatment can also be carried out in the dialysate system II instead of in the extracorporeal blood circuit I. These methods can be found in the prior art. The fistula flow can thus be determined by measuring the clearance during normal and reversed blood flow, for example.

In the case of hemofiltration, a device for processing dialysate and a dialysate feed line leading to the second compartment of the blood treatment unit are not required. Ultrafiltrate can be removed from the second compartment of the blood treatment unit via the dialysate removal line. In the case of a blood treatment in which diffusive or convective exchange does not take place, a second compartment and a dialysate supply line and removal line are not required either. All that is important for the invention is that the determination of the hemodynamic parameter should require a flow reversal. It is not important for the invention whether a physical or chemical characteristic variable is changed in the blood in order to determine the hemodynamic parameter. The physical or chemical characteristic variable can be measured on the blood side or on the dialysate side.

In the present embodiment, the device 17 for processing dialysate also functions as a device for changing a physical or chemical property of the blood. For this purpose, the device 17 for processing dialysate briefly changes the temperature or composition of the dialysate in the dialysate system II, which results in a change in a physical or chemical characteristic variable in the extracorporeal blood circuit I. The change in the physical or chemical property in the blood, for example the temperature of the blood (temperature bolus), is measured using the first or second measuring device 14A, 14B in the first and second blood line 5, 7. Alternatively, the hemodynamic parameter, in particular the shunt flow, can be determined from the progression of the conductivity of the dialysate, which can be measured using conductivity cells (not shown) in the dialysate feed line 18 and the dialysate removal line 19. Alternatively, the change in the physical or chemical property of the blood can also be brought about by means of external elements such as Peltier elements attached to the blood hose system or by means of infusing a physiological solution at an addition point located in the first or second blood line.

The direction of feed and the conveyance rate of the blood pump 10 can be controlled by the control and evaluation unit 12. The pressure values from the pressure sensors 13A, 13B can be used for this purpose, in order to determine and correct the effective blood flow, in a known manner, on the basis of the rotational speed of the pump and the negative pressure on the suction side in question.

The temporal progression of the physical or chemical property of the removed blood and of the returned blood is measured by the measuring devices 14A, 14B provided on the blood hose system, and transferred to the control and evaluation unit 12. The measuring devices 14A, 14B can for example be temperature sensors, optical or spectroscopic sensors or density sensors, for example ultrasound sensors. Likewise, conductivity measuring cells can be used to determine variables that correlate with the relevant physical or chemical properties of the blood. Instead of the physical or chemical characteristic variables on the blood side, physical or chemical characteristic variables on the dialysate side can also be measured, which variables correlate with the physical or chemical characteristic variables on the blood side. For this purpose, sensors for measuring the characteristic variables may be provided in the dialysate system II, for example in one or both dialysate lines 18 and 19.

In the present embodiment, the flow in the vascular access (shunt flow) is determined as the hemodynamic parameter. The shunt flow can be determined using the method that is described in detail in DE 195 28 907 A1.

The sequence of the shunt measurement is controlled by the control and evaluation unit 12. Initially, the blood pump 10 is operated in the "normal" conveying direction. The temperature or composition of the dialysate is briefly changed during "normal" blood flow. The temperature bolus or the jump in conductivity is transferred to the extracorporeal blood circuit I on account of the heat exchange at the dialyser. The measuring devices 14A, 14B in the first and second blood line 5, 7 detect the changes in the physical or chemical characteristic variable in the first and second blood line. The measured values are stored in a memory unit 12A of the control and evaluation unit 12. Then, the blood pump 10 is operated in the "reversed" conveying direction. The temperature or composition of the dialysate is briefly changed during "reversed" blood flow, and the temperature or composition of the dialysate in the first and second blood line is measured. The measured values are again stored in the memory unit 12A of the control and evaluation unit 12. The control and evaluation unit 12 then calculates the shunt flow on the basis of the measured values from the measuring devices and using suitable sequence control and a corresponding evaluation method, and displays the result on a display unit 20 or outputs the result via another means of communication, for example via a network. Possible error messages or instructions can also be communicated to the user on the display unit 20. Instead of a display unit, an alarm unit can also be provided, via which an acoustic or optical or tactile alarm is given, for example in the case of clogging of the filter. The evaluation method for calculating the shunt flow from the measured values is disclosed in DE 195 28 907 A1, to which reference is hereby explicitly made.

During the reversal of the flow direction, the control and evaluation unit 12 ensures that the protection devices 16A, 16B provided for the dialysis treatment are adjusted to the reversal of the blood flow direction. This relates in particular to the arterial and venous pressure monitoring, the significance of which is swapped when the flow reverses. Whereas a negative pressure prevails on the suction side of the blood pump ("arterial"), the pressure on the return side ("venous") is positive. At the same time, the venous pressure is used to detect possible needle disconnections. The control and evaluation unit is therefore designed such that the predetermined arterial and venous pressure threshold windows are swapped when the flow reverses. In normal operation, instead of the measured values from the venous sensor, the measured values from the arterial sensor are now evaluated using the algorithms for detecting a needle disconnection, which algorithms are based on a dynamic signal analysis and/or monitor the absolute failure to meet a lower pressure threshold on the return side. In addition, following the flow reversal, air infusion is monitored on the side that is the arterial side in normal operation.

In the present embodiment, the measurement is first carried out during a "normal" blood flow. However, it is also possible for the measurement to be first carried out when there is a "reversed" blood flow.

In the following, the structure of the apparatuses for catching the blood clots that are provided in the first and second blood line will be described in detail.

FIGS. 2A and 2B are simplified schematic cross sections through a first embodiment of the blood clot catcher 15A or 15B that operates in just one flow direction. In the opposite flow direction, the blood clot catcher is not operational, and therefore the flow resistance is lower. The flow direction is indicated by an arrow in FIGS. 2A and 2B.

The blood clot catcher comprises a preferably rotationally symmetric housing body 21 that has a first connection 22 and a second connection 23. The connections can be luer or luer lock connectors, or connecting pieces that are welded or adhesively bonded to the hose line portions 24, 25 of the blood hose system. A planar, circular screen body 26 comprising an annular retaining part 27 in which a circular screen 28 is inserted is located in the housing body 21 (FIG. 2C). The mesh size of the screen 28 is dimensioned such that blood clots are trapped. The outer diameter of the annular retaining part 27 is smaller than the inner diameter of the housing body 21, and therefore blood can flow around the sides of the retaining part 27 and/or the screen body 26. The screen body 26 is movably arranged in the centre of the housing body 21, in the flow path of the blood. For this purpose, the retaining part 27 is hung in the housing body 21 on flexible fixing elements 29, in particular threads, distributed around the periphery thereof. One end of each thread 29 is connected to the retaining part 27 and the other end of each thread is fastened to the wall of the housing body 21. The length of the threads 29 is dimensioned such that the screen body 26 can move freely in the centre of the housing body 21, between the first position, shown in FIG. 2A, and the second position, shown in FIG. 2B.

A valve seat 30 is formed in the housing body 21 on the side facing the second connection 23, on which valve seat the retaining part 27 of the screen body 26 rests in a sealing manner in the second position (FIG. 2A). No valve seat is formed in the housing body 21 on the side facing the first connection 22, and therefore blood can flow around the sides of the screen body 26 (FIG. 2B). The housing body 21 is funnel-shaped on the side of the valve seat 30, and is dome-shaped on the opposing side.

When the blood flows into the housing body 21 at the first connection 22, the screen body 26 moves into the second position on account of the dynamic pressure, and therefore the screen body 26 rests on the valve seat 30 and blood clots are trapped. When, in contrast, the blood flows into the housing body 21 at the second connection 23, the screen body 26 moves into the first position on account of the dynamic pressure, and therefore the blood flows around the screen body. This creates a flow path bypassing the screen body, and therefore the flow resistance is reduced.

The first blood clot catcher 15A is arranged in the first blood line 5 such that the portion of the first blood line 5 connected to the first patient connection 8 is connected to the second connection 23 of the housing body 21, and the portion of the first blood line 5 connected to the connection of the blood treatment unit 1 is connected to the first connection 22 of the housing body 21, such that the blood can flow past the filter screen 28 and through the first apparatus for catching blood clots 15A in the "normal" flow direction, but blood clots are trapped in the "reversed" flow direction.

The second blood clot catcher 15B is arranged in the second blood line 7 such that the portion of the second blood line 7 connected to the second patient connection 9 is connected to the second connection 23 of the housing body 21, and the portion of the second blood line 7 connected to the connection of the blood treatment unit 1 is connected to the first connection 22 of the housing body 21, such that blood clots are trapped by the second blood clot catcher 15B in the "normal" flow direction, but the blood can flow past the filter screen 28 in the "reversed" flow direction.

FIGS. 3A and 3B are simplified schematic cross sections through a second embodiment of the blood clot catcher, which differs from the first embodiment in the design of the housing body 21 and of the screen body 26. The corresponding parts are provided with the same reference signs. In the second embodiment, the preferably rotationally symmetric housing body 21 of the blood clot catcher is elongate, the housing body being conical on the side facing the first connection 22 and ovoid on the side facing the second connection 23. In the second embodiment, the screen 28 of the screen body 26 is designed in the shape of a thimble, and therefore the screen surface is increased.

The design of the housing body 21 and of the screen body 26 of the blood clot catcher 15A, 15B is not limited to the shapes described above. Housing bodies and screen bodies can also be of any other shape, provided that a flow path bypassing the screen body is created in the opposite flow direction.

The invention claimed is:

1. An apparatus for extracorporeal blood treatment, the apparatus comprising:
    a blood treatment unit that comprises at least one compartment;
    a first blood line connected to a first connection of the compartment and comprising a first patient connection;
    a second blood line connected to a second connection of the compartment and comprising a second patient connection;
    at least one screen for catching blood clots provided at least in the first blood line;
    a blood pump configured to convey blood;
    a device configured to measure a physical or chemical characteristic variable of blood flow during a normal blood flow and configured to measure a physical or chemical characteristic variable of blood flow during a reversed blood flow; and
    a control and evaluation unit connected to the blood pump and to the device configured to measure a physical or chemical characteristic variable, wherein
    the control and evaluation unit is configured to control the blood pump to operate in a first operating mode to provide the normal blood flow such that blood flows from the first patient connection to the blood treatment unit and from the blood treatment unit to the second patient connection, and to operate in a second operating mode to provide the reversed blood flow such that the blood flows from the second patient connection to the blood treatment unit and from the blood treatment unit to the first patient connection, and
    the control and evaluation unit is configured to determine a hemodynamic parameter from a measured physical or chemical characteristic variable obtained during the normal blood flow and from a measured physical or chemical characteristic variable obtained during the reversed blood flow.

2. An apparatus for extracorporeal blood treatment, the apparatus comprising:
    a blood treatment unit that comprises at least one compartment;
    a first blood line connected to a first connection of the compartment and comprising a first patient connection;
    a second blood line connected to a second connection of the compartment and comprising a second patient connection;
    at least one apparatus for catching blood clots provided at least in the first blood line;
    a blood pump configured to convey blood;
    a device configured to measure a physical or chemical characteristic variable; and
    a control and evaluation unit connected to the blood pump and to the device configured to measure a physical or chemical characteristic variable, wherein
    the control and evaluation unit is configured to control the blood pump to operate in a first operating mode to provide a normal blood flow such that blood flows from the first patient connection to the blood treatment unit and from the blood treatment unit to the second patient connection, and to operate in a second operating mode to provide a reversed blood flow such that the blood flows from the second patient connection to the blood treatment unit and from the blood treatment unit to the first patient connection, a hemodynamic parameter is determined from a measured physical or chemical characteristic variable that is measured during the normal blood flow and from a measured physical or chemical characteristic variable that is measured during the reversed blood flow, and the at least one apparatus for catching blood clots comprises a housing body having a first connection and a second connection, and a screen body for catching the blood clots and being arranged between the first connection and the second connection in the flow path of the blood, the at least one apparatus for catching blood clots being designed such that a flow path bypassing the screen body forms in the housing body when blood flows in at the second connection and out at the first connection, and a flow path bypassing the screen body does not form when blood flows in at the first connection and out at the second connection.

3. The apparatus for extracorporeal blood treatment according to claim 2, wherein the screen body is designed as a valve body, and a valve seat for the screen body is formed in the housing body, the screen body being movably arranged in the housing body such that the screen body (1) rests on the valve seat when blood flows in at the first connection and out at the second connection, and (2) is lifted off of the valve seat when blood flows in at the second connection and out at the first connection, such that a flow path bypassing the screen body forms in the housing body.

4. The apparatus for extracorporeal blood treatment according to claim 3, wherein the screen body is movably arranged between the first connection and the second connection in the flow path of the blood, the movement of the screen body in the housing body being restricted to a range between a first end position and a second end position.

5. The apparatus for extracorporeal blood treatment according to claim 4, wherein the screen body is fixed to the housing body between the first connection and the second connection in the flow path of the blood by means of elongate, flexible fixing elements, one end of each of which fixing elements is connected to the screen body and the other end of each of which fixing elements is connected to the housing body, the fixing elements being arranged around the periphery of the screen body.

6. The apparatus for extracorporeal blood treatment according to claim 2, wherein the housing body has a circular cross section and the screen body comprises a retaining part having a circular cross section, in which retaining part a screen is inserted.

7. The apparatus for extracorporeal blood treatment according to claim 6, wherein the screen is designed as a planar, discoid body or in the shape of a thimble.

8. The apparatus for extracorporeal blood treatment according to claim 2, wherein a portion of the first blood line connected to the first patient connection is connected to the second connection of the housing body of the at least one apparatus for catching blood clots, and a portion of the first blood line connected to the connection of the blood treatment unit is connected to the first connection of the housing body of the at least one apparatus for catching blood clots.

9. The apparatus for extracorporeal blood treatment according to claim 2, wherein the at least one apparatus for catching blood clots comprises a first apparatus for catching blood clots and a second apparatus for catching blood clots, the first apparatus for catching blood clots is provided in the first blood line and the second apparatus for catching blood clots is provided in the second blood line, a portion of the second blood line connected to the blood treatment unit is connected to the first connection of the housing body of the second apparatus for catching blood clots, and a portion of the second blood line connected to the second patient connection is connected to the second connection of the housing body of the second apparatus for catching blood clots.

10. The apparatus for extracorporeal blood treatment according to claim 1, further comprising a first pressure sensor for measuring the pressure in the first blood line, wherein the first pressure sensor is connected to the control and evaluation unit such that the control and evaluation unit receives measured values from the first pressure sensor, the control and evaluation unit is designed such that pressure measured by the first pressure sensor in the second operating mode is compared with a predetermined threshold value, and a signal is generated when the pressure measured by the first pressure sensor exceeds the predetermined threshold value.

11. The apparatus for extracorporeal blood treatment according to claim 1, further comprising a first pressure sensor for measuring pressure in the first blood line, and a second pressure sensor for measuring pressure in the second blood line, wherein the first pressure sensor and the second pressure sensor are connected to the control and evaluation unit such that the control and evaluation unit receives measured values from the first pressure sensor and from the second pressure sensor, the control and evaluation unit is designed such that the pressure measured by the first pressure sensor in the second operating mode is compared with the pressure measured by the second pressure sensor in the first operating mode, and a signal is generated when the pressure measured by the first pressure sensor exceeds the pressure measured by the second pressure sensor by a predetermined amount or factor.

12. The apparatus for extracorporeal blood treatment according to claim 11, wherein the control and evaluation unit is designed such that the blood pump is switched from the reversed blood flow to the normal blood flow when the signal is generated.

13. The apparatus for extracorporeal blood treatment according to claim 11, wherein an alarm unit and/or a display unit is connected to the control and evaluation unit such that the alarm unit and/or the display unit receives the signal when the signal is generated.

14. An apparatus for catching blood clots in a blood line for supplying or removing blood in a blood treatment unit of an extracorporeal blood treatment apparatus, the apparatus comprising:
a housing body having a first connection and a second connection; and
a screen body for catching the blood clots, which is arranged between the first connection and the second connection in the flow path of blood in the blood line, wherein
the apparatus for catching blood clots is designed such that a flow path bypassing the screen body forms in the housing body when blood flows in at the second connection and out at the first connection, and a flow path bypassing the screen body does not form when blood flows in at the first connection and out at the second connection.

15. The apparatus according to claim 14, wherein the screen body is designed as a valve body, a valve seat for the screen body is formed in the housing body, the screen body is movably arranged in the housing body such that the screen body rests on the valve seat when blood flows in at the first connection and out at the second connection, and the screen body is lifted off of the valve seat when blood flows in at the second connection and out at the first connection such that a flow path bypassing the screen body forms in the housing body.

16. The apparatus according to claim 15, wherein the screen body is movably arranged between the first connection and the second connection in the flow path of the blood, and the movement of the screen body in the housing body is restricted to a range between a first end position and a second end position.

17. The apparatus according to claim 16, wherein the screen body is fixed to the housing body between the first connection and the second connection in the flow path of blood in the blood line by means of elongate, flexible fixing elements, one end of each of which fixing elements is connected to the screen body and the other end of each of which fixing elements is connected to the housing body, the fixing elements being arranged around the periphery of the screen body.

18. The apparatus according to claim 17, wherein the housing body has a circular cross section, the screen body comprises a retaining part having a circular cross section, and a screen is inserted in the retaining part.

19. The apparatus according to claim 18, wherein the retaining part is designed having the screen as a planar body or in the shape of a thimble.

20. A method for determining a hemodynamic parameter during extracorporeal blood treatment using an extracorporeal blood treatment apparatus, the extracorporeal blood treatment apparatus comprising:
a blood treatment unit that comprises at least one compartment;
a first blood line connected to the compartment and comprising a first patient connection;
a second blood line connected to the compartment and comprising a second patient connection; and
a blood pump for conveying blood,
the method comprising
operating the blood pump in a first operating mode to provide a normal blood flow such that blood flows from the first patient connection to the blood treatment unit and from the blood treatment unit to the second patient connection,
measuring a physical or chemical characteristic variable during operation in the first operating mode,
operating the blood pump in a second operating mode to provide a reversed blood flow such that the blood flows from the second patient connection to the blood treatment unit and from the blood treatment unit to the first patient connection,
measuring a physical or chemical characteristic variable during operation in the second operating mode, and
determining a hemodynamic parameter from the measured physical or chemical characteristic variable during operation in the second operating mode, wherein, following a reversal of the flow direction of the blood, blood clots that have formed in the blood upstream of the compartment of the blood treatment unit before the reversal of the flow direction of the blood are trapped by an apparatus for catching blood clots, in the first blood line.

21. An apparatus for extracorporeal blood treatment, the apparatus comprising:
a blood treatment unit that comprises at least one compartment;
a first blood line connected to a first connection of the compartment and comprising a first patient connection;
a second blood line connected to a second connection of the compartment and comprising a second patient connection;
at least one screen for catching blood clots, provided in at least the first blood line;
a blood pump configured to convey blood;
a device configured to measure a physical or chemical characteristic variable; and
a control and evaluation unit connected to the blood pump and to the device configured to measure a physical or chemical characteristic variable, wherein
the control and evaluation unit is configured to control the blood pump to operate in a first operating mode to provide a normal blood flow such that blood flows from the first patient connection to the blood treatment unit and from the blood treatment unit to the second patient connection, and to operate in a second operating mode to provide a reversed blood flow such that blood flows from the second patient connection to the blood treatment unit and from the blood treatment unit to the first patient connection,
the control and evaluation unit is configured to determine a hemodynamic parameter from a measured physical or chemical characteristic variable measured during the normal blood flow, and from a measured physical or chemical characteristic variable measured during the reversed blood flow, and
the hemodynamic parameter is shunt flow.

* * * * *